United States Patent [19]

Berns

[11] Patent Number: 4,595,491
[45] Date of Patent: Jun. 17, 1986

[54] PROCESS FOR THE SEPARATION OF AROMATIC HYDROCARBONS FROM A HYDROCARBON MIXTURE OF VARYING AROMATIC CONTENT

[75] Inventor: Horst Berns, Mülheim, Fed. Rep. of Germany

[73] Assignee: Krupp-Koppers GmbH, Essen, Fed. Rep. of Germany

[21] Appl. No.: 708,344

[22] Filed: Mar. 5, 1985

[30] Foreign Application Priority Data

Mar. 14, 1984 [DE] Fed. Rep. of Germany ....... 3409307

[51] Int. Cl.$^4$ ............................................. C10G 21/20
[52] U.S. Cl. ..................................... 208/326; 208/313
[58] Field of Search ............... 208/313, 326, 321, 323, 208/314

[56] References Cited

U.S. PATENT DOCUMENTS 3,207,092  9/1965  Van Kleef et al. ................. 208/313
3,210,269 10/1965  Kosters et al. ..................... 208/313
3,435,087  3/1969  Broughton .......................... 208/321
3,470,088  9/1969  Vickers .............................. 208/321

FOREIGN PATENT DOCUMENTS 1568940  6/1970  Fed. Rep. of Germany .

Primary Examiner—Andrew H. Metz
Assistant Examiner—Glenn A. Caldarola
Attorney, Agent, or Firm—Michael J. Striker

[57] ABSTRACT

A process is disclosed for the separation of an aromatic hydrocarbon from a hydrocarbon mixture of varying aromatic content, by means of extractive distillation, employing as a selective solvent, an N-substituted morpholine, wherein the N-substituent contains up to 7 carbon atoms. In the entry product, the weight ratio of light non-aromatic hydrocarbons to heavy non-aromatic hydrocarbon should amount to at least 0.4 to 1. The light non-aromatic hydrocarbon necessary for adjustment of this ratio can be either introduced directly into the lower part of the extractive distillation column, or added to the entry product before introducing the latter to the extractive distillation column.

8 Claims, 1 Drawing Figure

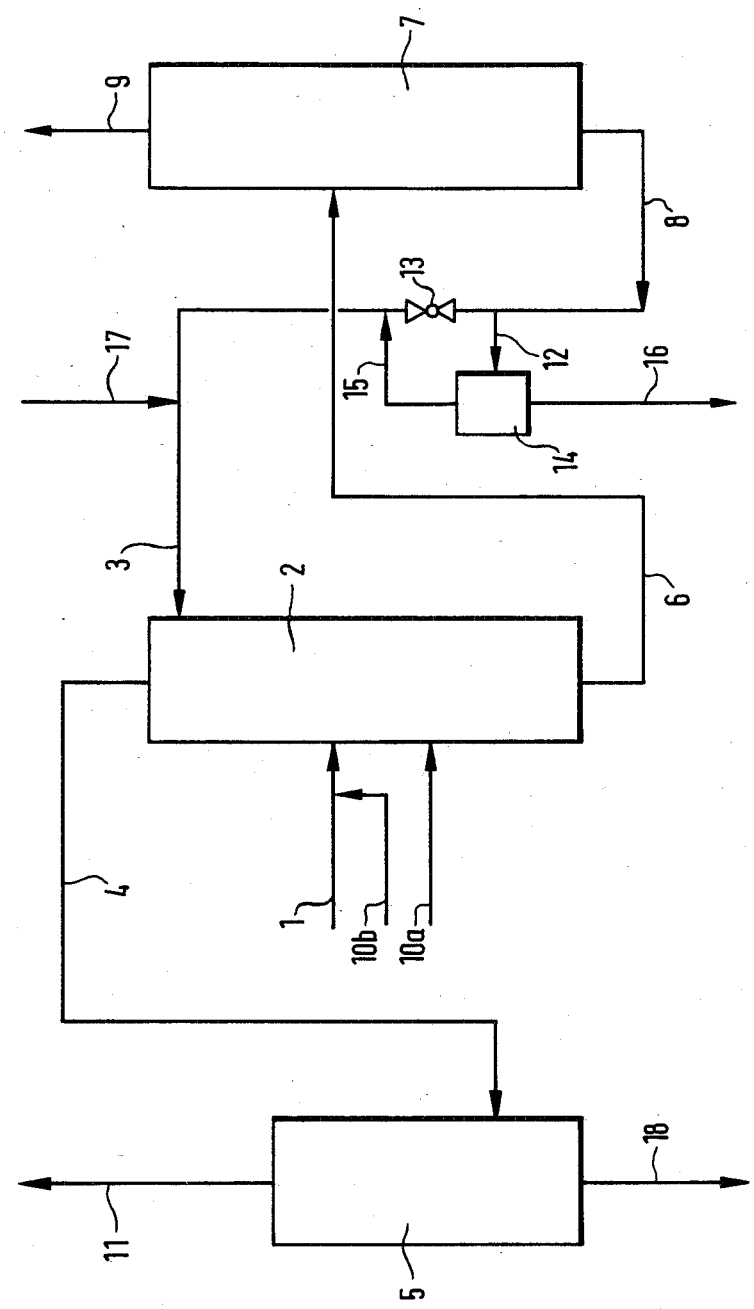

ered. Analogously all non-aromatic hydrocarbons whose boiling points are no
PROCESS FOR THE SEPARATION OF AROMATIC HYDROCARBONS FROM A HYDROCARBON MIXTURE OF VARYING AROMATIC CONTENT

FIELD OF THE INVENTION

This invention relates to a process for the separation of an aromatic hydrocarbon from a hydrocarbon mixture of varying aromatic content.

BACKGROUND OF THE INVENTION

There are various processes known in the art for the recovery of aromatic hydrocarbons from hydrocarbon mixtures. In West German Off. No. 1,568,940, a typical recovery process is disclosed. Such processes have been employed in various large-scale technical projects, and have been successful. Nonetheless, it has been demonstrated that in the working up of certain entry products, such as a crude benzene fraction obtained from pyrolysis benzene, in spite of proper maintenance procedures, fluctuations still occur in the yield of the aromatic hydrocarbon, as well as in the purity thereof. No plausible explanation has been provided.

Whether or not the fluctuations in the product yield or purity have been relatively small, such a problem still represents a significant drawback for any large-scale operation. Not only is the purity of the product open to question but also the yield of aromatic hydrocarbon and/or the energy consumption of the process must be considered.

Thus, for example, where a crude benzene fraction obtained from pyrolysis benzene is worked-up for benzene recovery, not only does the non-aromatic hydrocarbon content of the benzene product fluctuate, but furthermore the non-aromatic hydrocarbon fraction separated from the benzene still contains a significant benzene content. Simultaneously, temperature fluctuations occur in the regulating plates of an extractive distillation column.

OBJECTS OF THE INVENTION

It is an object of the invention to improve the process for recovery of an aromatic hydrocarbon from a hydrocarbon mixture of varying aromatic content.

It is a further object of the invention to provide a process where the aromatic hydrocarbon is recovered in high purity and yield.

SUMMARY OF THE INVENTION

According to the invention fluctuations in the non-aromatic hydrocarbon content of the aromatic hydrocarbon product are substantially avoided. Furthermore the yield and purity of the aromatic hydrocarbon product are optimized.

The present process for the separation of an aromatic hydrocarbon from a hydrocarbon mixture of varying aromatic content employs extractive distillation with an N-substituted-morpholine as the selective solvent. The N-substituted-morpholine has an N-substituent containing no more than 7 carbon atoms.

According to the extractive distillation process, the content of the heavy non-aromatic hydrocarbons in the distillation column and having boiling points which lie at least 14° C. above the boiling point of the pure aromatic hydrocarbon to be obtained, is maintained in proportion to the content of the light non-aromatic hydrocarbons, the boiling points of which lie at least 38° C. below the boiling point of the desired aromatic hydrocarbon product. According to the invention, the weight ratio between the light non-aromatic hydrocarbons and the heavy non-aromatic hydrocarbons should be at least 0.4 to 1.

It has been discovered that a relationship exists between the content of heavy non-aromatic hydrocarbons and light non-aromatic hydrocarbons in the entry product. Such a relationship influences the purity of the product as well as the running of the plant itself. Which non-aromatic hydrocarbons are considered to be heavy, and which are considered to be light are determined on the basis of the boiling points of these compounds. According to the definitions set forth hereinabove, the designations heavy non-aromatic hydrocarbon and light non-aromatic hydrocarbon are dependent upon the boiling point of the particular pure aromatic hydrocarbon to be recovered.

For example, according to the present invention, if exclusively pure benzene (m.p. approximately 80° C.) is to be recovmore than 42° C. are considered as light non-aromatic hydrocarbons. For the recovery of aromatic hydrocarbons such as toluene or xylene, these boiling point limits for the light and heavy non-aromatic hydrocarbons are displaced, corresponding to the particular boiling point of toluene or xylene. For the sake of simplicity, only the collective designations heavy non-aromatic hydrocarbon and light non-aromatic hydrocarbon are employed in the description of the process.

It has been proved, upon the basis of thorough testing, that the heavy non-aromatic hydrocarbons can be extensively driven off from the aromatic hydrocarbon fraction during the extractive distillation as an extract in the sump of the extractive distillation column, when the light non-aromatic hydrocarbons are present in the entry product to a sufficient extent. The light non-aromatic hydrocarbons in this case are paraffins having one carbon atom less than the number of carbon atoms present in the aromatic hydrocarbon to be recovered. These light non-aromatic hydrocarbons act as a stripping vapor and thus provide for the driving off of the heavy non-aromatic hydrocarbons from the aromatic hydrocarbon fraction located in the sump of the extractive distillation column. Furthermore the light non-aromatic hydrocarbons provide the non-aromatic hydrocarbon mixture in the upper part of the extractive distillation column with a low dew point. In order to guarantee these conditions, it is necessary that the abovementioned weight ratio of light non-aromatic hydrocarbons to heavy non-aromatic hydrocarbons in the entry product be maintained according to the present invention.

If the correct weight ratio is not already provided in the entry product initially, it is necessary to adjust the weight ratio by adding light non-aromatic hydrocarbons. The light non-aromatic hydrocarbons can be led into the bottom part of the extractive distillation column underneath the point where the entry product is delivered. The light non-aromatic compounds may be in liquid or in vapor form. Alternatively the light non-aromatic hydrocarbons can be added to the entry product before it is channeled to the extractive distillation column. If excess light non-aromatic hydrocarbon is present in the entry product, in principle this should be no detriment. However, it must be remembered that the light non-aromatic hydrocarbons must be driven off during the extractive distillation across the top of the extractive distillation column. The light non-aromatic hydrocarbons influence the characteristics of the other non-aromatic hydrocarbons by increasing the vapor pressure for example. Therefore it is advantageous to set an upper limit on the addition of the light non-aromatic hydrocarbons to the entry product. The upper limit should be set so that the maximum ratio of light non-aromatic hydrocarbons to heavy non-aromatic hydrocarbons in the entry product should be no more than 5 to 1.

The light non-aromatic hydrocarbons which are added to the process for adjusting the weight ratio of the light non-aromatic hydrocarbons to the heavy non-aromatic hydrocarbons can be partially or completely recovered from the top product vapors of the extractive distillation column by means of appropriate partial condensation, followed by recycle to the feed point in the extractive distillation.

BRIEF DESCRIPTION OF THE DRAWING

The sole FIGURE in this application is a flow diagram of the arrangement employed to carry out extractive distillation according to the invention.

DETAILED DESCRIPTION OF THE DRAWING

Referring to the FIGURE, the hydrocarbon mixture to be separated, which is the entry product, is introduced by means of conduit 1 into the middle part of the extractive distillation column 2, provided with plates or similar components. In connection therewith, the entry product is either heated, before its introduction into the extractive distillation column 2, to a temperature just below its boiling point, or the entry product is introduced already in a partially evaporated state into the extractive distillation column 2. By means of the conduit 3, the selective solvent is supplied to the top of the extractive distillation column 2, after which said solvent flows down across the components of this column, whereby said solvent selectively removes the vaporous aromatic hydrocarbons. The non-aromatic hydrocarbons escape by means of conduit 4 at the top of this column, and can be partially condensed in the condenser 5. The liquid sump product of the extractive distillation column (extract) is comprised of this extracted solvent and the aromatic hydrocarbons dissolved therein, and is discharged by means of conduit 6 from the extractive distillation column 2, after which it is led into column 7 in which the aromatic hydrocarbon is distillatively separated from the selective solvent. The selective solvent is removed from the column sump by means of conduit 8, after which it is led back into the extractive distillation column 2 across conduit 3, whereas the aromatic hydrocarbon vapors escape across the top from column 7 by means of conduit 9, and are then condensed in a non-represented condensation arrangement.

The addition of the necessary light non-aromatic hydrocarbons follows across conduit 10a or 10b. Here is also where any light non-aromatic hydrocarbons recovered by means of partial condensation are recycled to the feed point from conduit 11. Since over a period of time, the selective solvent can become contaminated with impurities, a branch conduit 12 is provided in the area of conduit 8, through which branch conduit a partial amount of the selective solvent can be led to the regeneration arrangement 14, upon appropriate positioning of valve 13. The regenerated solvent is recycled into circulation (i.e. conduit 3) by means of conduit 15, whereas the separated impurities are discharged from the regeneration arrangement 14 by means of conduit 16. Conduit 17 serves as the supply of fresh solvent.

The non-aromatic hydrocarbons which have not been discharged across conduit 11 and recycled to the extractive distillation column 2 are removed from the condenser 5 and then optionally introduced to an aftertreatment, through conduit 18.

Obviously, upon practical employment of the process according to the present invention, certain variations from the above described manner of operation of the extractive distillation are possible. Such variations, however, are not related to the specific features of the present invention, and therefore require no further discussion.

The effectiveness of the process according to the present invention is clearly substantiated by means of the following comparative tests. For these tests, an entry product is employed which constitutes a crude benzene fraction recovered by pyrolysis benzene, having the following composition:

TABLE 1

| | B.P. | % wt. |
|---|---|---|
| $\Sigma$ i-pentane | 9.5 to 28.9° C. | 0.12 |
| n-pentane | 36.1° C. | 0.08 |
| | (light non-aromatic hydrocarbons) = | 0.20 |
| n-heptane | 98.4° C. | 0.52 |
| 1-cis-2-dimethylcyclopentane | 99.5° C. | 0.03 |
| methylcyclohexane | 100.9° C. | 0.13 |
| ethylcyclopentane | 103.4° C. | 0.03 |
| | (heavy non-aromatic hydrocarbons) = | 0.71 |
| benzene | 80.1° C. | 74.18 |
| | $\Sigma =$ | 75.09 |

The residual 24.91% by weight comprises non-aromatic hydrocarbons boiling at temperatures between the boiling temperatures of the light and the heavy non-aromatic hydrocarbons.

With this entry product, separated from the pure benzene by means of extractive distillation using N-formyl-morpholine as the selective solvent, four comparative tests were performed with maintenance of analogous process conditions. Herewith Test 1 is performed without any further addition of light non-aromatic hydrocarbons, whereas in Tests 2,3 and 4, in each case an increased amount of $C_5$ non-aromatic hydrocarbons (pentanes) is added. The results are summarized in the following Table 2:

TABLE 2

| Test No. | 1 | 2 | 3 | 4 |
|---|---|---|---|---|
| $C_5$-addition to 100 parts entry product to the ED column | 0.00 | 0.25 | 1.50 | 1.70 |

TABLE 2-continued

| Test No. | 1 | 2 | 3 | 4 |
|---|---|---|---|---|
| Heavy non-aromatics in entry product : Light non-aromatics in entry product | 1:0.28 | 1:0.63 | 1:2.43 | 1:2.72 |
| t heating vapor in the ED column t pure benzene | 0.191 | 0.190 | 0.191 | 0.191 |
| Benzene content of non-aromatics | 9.60% | 8.10% | 6.10% | 4.80% |
| $C_5$ content of the non-aromatics | 0.70% | 1.59% | 5.93% | 6.68% |
| Non-aromatics content of the pure benzene | 0.108% | 0.098% | 0.074% | 0.060% |
| $\frac{\text{Pure benzene product}}{\text{benzene in entry product}} \times 100 =$ (yield) | 96.41% | 97.00% | 97.68% | 98.19% |

A comparison of the test results shows that with increased addition of light non-aromatic hydrocarbons to the entry product, not only the purity of the recovered fractions (aromatic and non-aromatic hydrocarbons) but also the aromatic hydrocarbon (benzene) yield is improved, without any occurrence therewith of an increase in the heating vapor requirements of the extractive distillation column. The advantages of the process according to the present invention have thus been clearly proved.

It will be understood that each of the elements described above, or two or more together, may also find a useful application in other types of separations differing from the types described above.

While the invention has been illustrated and described as directed to a process for the separation of aromatic hydrocarbons from a hydrogen mixture of varying aromatic hydrocarbon content, it is not intended to be limited to the details shown, since various modifications and structural changes may be made without departing in any way from the spirit of the present invention.

Without further analysis, the foregoing will so fully reveal the gist of the present invention, that others can, by applying current knowledge, readily adapt it for various applications without omitting features that, from the standpoint of the prior art, fairly constitute essential characteristics of the generic or specific aspects of the invention.

I claim:

1. A process for the separation of an aromatic hydrocarbon from a hydrocarbon mixture of varying aromatic content which comprises the steps of:
   (a) introducing into a distillation column a hydrocarbon mixture containing an aromatic hydrocarbon, heavy non-aromatic hydrocarbons the boiling points of which lie at least 14° C. above the boiling point of the pure aromatic compound to be recovered, and light non-aromatic hydrocarbons the boiling points of which lie at least 38° C. below the boiling point of the pure aromatic compound to be recovered, whereby the weight ratio of the light non-aromatic hydrocarbons to the heavy non-aromatic hydrocarbons amounts to at least 0.4 to 1;
   (b) adding as a selective solvent to the top of the distillation column an N-substituted-morpholine wherein the substituent has up to 7 carbon atoms to contact vapors of said hydrocarbon mixture introduced according to step (a); and
   (c) extractively distilling said hydrocarbon mixture to vaporize the non-aromatic hydrocarbons thus forming a head product and to collect the aromatic hydrocarbon dissolved in the selective solvent as a liquid sump product.

2. The process defined in claim 1 wherein the non-aromatic hydrocarbons are paraffins or cycloparaffins.

3. The process defined in claim 1, wherein in step (a) the weight ratio of the light non-aromatic hydrocarbons to the heavy non-aromatic hydrocarbons is maintained by further introducing light non-aromatic hydrocarbons in liquid or vapor form into the lower part of the distillation column beneath the point where the hydrocarbon mixture is introduced, or adding said light non-aromatic hydrocarbons to the hydrocarbon mixture before entry of the latter into the distillation column.

4. The process defined in claim 3 wherein the introduction of light non-aromatic hydrocarbons is so limited that a weight ratio of the light non-aromatic hydrocarbons to the heavy non-aromatic hydrocarbons is no greater than 5 to 1.

5. The process defined in claim 3 further comprising the step of completely or partially recovering the light non-aromatic hydrocarbons introduced into the lower part of the distillation column, as top product vapors.

6. The process defined in claim 1 further comprising the step of withdrawing the liquid sump product from step (c), and separately distilling said liquid sump product to separate the aromatic hydrocarbon from the selective solvent.

7. The process defined in claim 6 further comprising the step of regenerating the selective solvent separated from the aromatic hydrocarbon, and recycling the regenerated selective solvent to the distillation column to separate more aromatic hydrocarbon from the hydrocarbon mixture.

8. The process defined in claim 1 wherein the aromatic hydrocarbon is benzene, the light non-aromatic hydrocarbons include n-pentane and isopentane, the heavy non-aromatic hydrocarbons include n-heptane, 1-cis-2-dimethylcyclopentane, methylcyclohexane, and ethylcyclopentane, and the selective solvent is N-formyl-morpholine.

* * * * *